United States Patent
Seo et al.

(10) Patent No.: US 9,919,533 B2
(45) Date of Patent: Mar. 20, 2018

(54) LIQUID DROPLET FORMING APPARATUS

(71) Applicants: Manabu Seo, Kanagawa (JP); Satoshi Nakazawa, Kanagawa (JP); Yuzuru Kuramochi, Tokyo (JP); Daisuke Takagi, Kanagawa (JP); Takahiko Matsumoto, Kanagawa (JP)

(72) Inventors: Manabu Seo, Kanagawa (JP); Satoshi Nakazawa, Kanagawa (JP); Yuzuru Kuramochi, Tokyo (JP); Daisuke Takagi, Kanagawa (JP); Takahiko Matsumoto, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 15/335,040

(22) Filed: Oct. 26, 2016

(65) Prior Publication Data

US 2017/0120604 A1    May 4, 2017

(30) Foreign Application Priority Data

Oct. 30, 2015  (JP) .................................. 2015-214102
Oct. 24, 2016  (JP) .................................. 2016-207746

(51) Int. Cl.
*B41J 2/17*          (2006.01)
*G01N 15/06*     (2006.01)
(Continued)

(52) U.S. Cl.
CPC ......... *B41J 2/1707* (2013.01); *B41J 2/14201* (2013.01); *B41J 2/16579* (2013.01);
(Continued)

(58) Field of Classification Search
CPC ..... B41J 2/1707; B41J 2/04561; G01N 21/49; G01N 15/06; G01N 2015/0693
See application file for complete search history.

(56) References Cited

U.S. PATENT DOCUMENTS 5,518,179 A      5/1996  Humberstone et al.
2011/0019524 A1*  1/2011  Nakata ................ G11B 7/0909
                                                    369/112.23
(Continued)

FOREIGN PATENT DOCUMENTS

JP       63172943 A  *  7/1988
JP       2849647         1/1999
(Continued)

OTHER PUBLICATIONS

Yamaguchi et al., Piezoelectric Inkjet-based One Cell per One Droplet Automatic Printing by Image Processing, Nov. 2013, IEEE/RSJ, pp. 502-507.*

(Continued)

*Primary Examiner* — Sharon A Polk
(74) *Attorney, Agent, or Firm* — Oblon, McClelland, Maier & Neustadt, L.L.P.

(57) ABSTRACT

A liquid droplet forming apparatus includes a liquid retention unit configured to retain particle suspension liquid in which precipitated particles are suspended; a membrane member, in which a nozzle is formed, configured to discharge the particle suspension liquid retained in the liquid retention unit, as a liquid droplet, by vibration from the nozzle; and a particle state detection unit configured to detect, from a side of the liquid retention unit, a particle state of the precipitated particle around the nozzle in the particle suspension liquid.

9 Claims, 12 Drawing Sheets

(51) Int. Cl.
 *B41J 2/14* (2006.01)
 *B41J 2/165* (2006.01)
(52) U.S. Cl.
 CPC ..... *G01N 15/06* (2013.01); *B41J 2002/14354* (2013.01); *B41J 2202/15* (2013.01); *G01N 2015/0693* (2013.01)

(56) References Cited

U.S. PATENT DOCUMENTS

2013/0037623 A1   2/2013  Yamaguchi
2015/0035884 A1*  2/2015  Gengrinovich ...... B41J 2/04581
                                                           347/10
2016/0175834 A1   6/2016  Seo et al.

FOREIGN PATENT DOCUMENTS

| JP | 4013869 | 11/2007 |
|---|---|---|
| JP | 5716213 | 5/2015 |
| JP | 2016-116489 | 6/2016 |
| WO | 2011/099287 | 8/2011 |

OTHER PUBLICATIONS

"Technology of tissue culture" Japanese Tissue Culture Association, 3$^{rd}$ edition, Jun. 1996, pp. 581-583 (with English language translation).

\* cited by examiner

LIQUID DROPLET FORMING APPARATUS

CROSS-REFERENCE TO RELATED APPLICATIONS

The present application claims benefit of priority under 35 U.S.C. § 119 of Japanese Patent Applications No. 2015-214102, filed Oct. 30, 2015, and No. 2016-207746, filed Oct. 24, 2016. The contents of these applications are incorporated herein by reference in their entirety.

BACKGROUND OF THE INVENTION

1. Field of the Invention

The disclosure herein generally relate to a liquid droplet forming apparatus.

2. Description of the Related Art

Recently, in accordance with a development of stem cell technology, a technique has been developed in which an organization body is formed by discharging a plurality of cells by inkjet. As the type of inkjet apparatus, a piezoelectric pressure type using a piezoelectric element, a thermal type using a heater, an electrostatic type in which liquid is attracted by an electrostatic attraction or the like may be used. Among these, the piezoelectric pressure type is preferred to be used for forming a droplet of a cell suspension because damage due to heat or an electrical field is harder to be caused to cells by this type compared with other types.

Upon discharging a droplet including particulate matter represented by a cell, detecting how much the discharged liquid droplet includes particles is important. Therefore, various methods of detecting a number of particles included in the discharged liquid droplet have been proposed.

For example, regarding an inkjet apparatus that pressurizes a liquid chamber (cavity) by a piezoelectric element (actuator) to form a liquid droplet from a nozzle, a technique of detecting a number and a form of granular bodies included in a liquid between the cavity and the nozzle from a side is disclosed (See, for example, WO 2011/099287). Therefore, a particle in the discharged liquid droplet can be recognized.

Another example discloses a technique of observing a liquid droplet discharged from a dispensing element including an inkjet element or the like from a side, and identifying a state of the liquid droplet and a trajectory (See, for example, Japanese Patent No. 4013869).

SUMMARY OF THE INVENTION

It is a general object of at least one embodiment of the present invention to provide a liquid droplet forming apparatus that substantially obviates one or more problems caused by the limitations and disadvantages of the related art.

In one embodiment, a liquid droplet forming apparatus includes a liquid retention unit configured to retain particle suspension liquid in which precipitated particles are suspended; a membrane member, in which a nozzle is formed, configured to discharge the particle suspension liquid retained in the liquid retention unit, as a liquid droplet, by vibration from the nozzle; and a particle state detection unit configured to detect, from a side of the liquid retention unit, a particle state of the precipitated particle around the nozzle in the particle suspension liquid.

BRIEF DESCRIPTION OF THE DRAWINGS

Other objects and further features of embodiments will become apparent from the following detailed description when read in conjunction with the accompanying drawings, in which.

DESCRIPTION OF THE PREFERRED EMBODIMENTS

Figure 1:
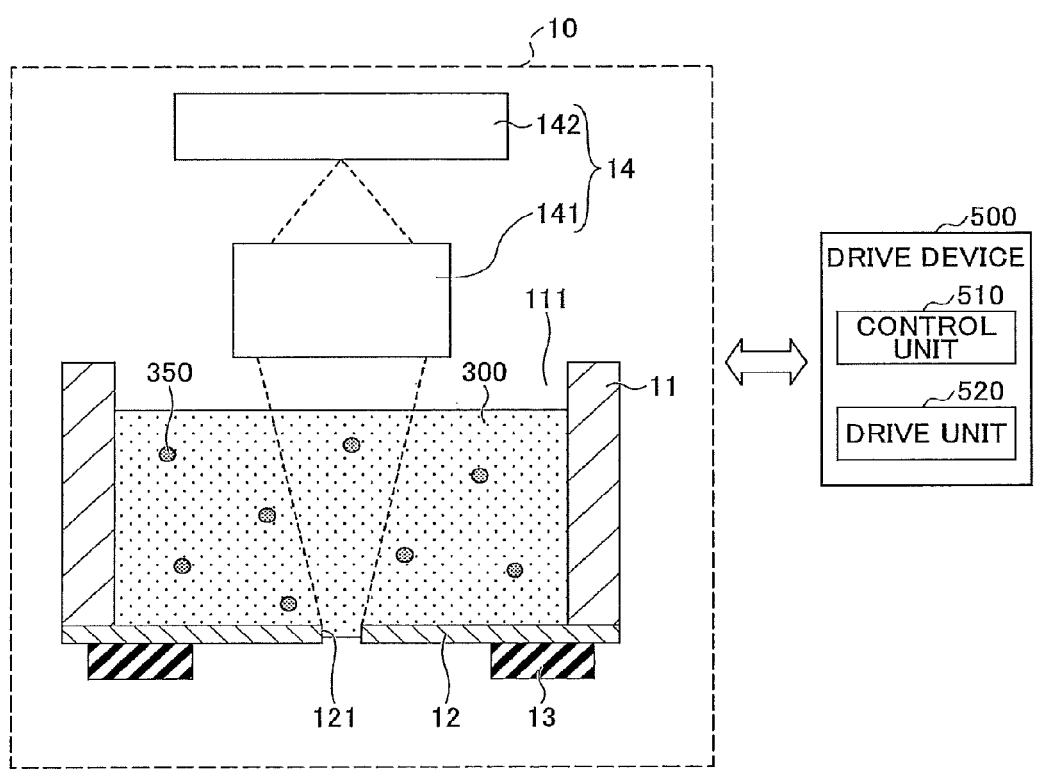
FIG. 1 is a diagram schematically depicting an example of a liquid droplet forming apparatus according to a first embodiment.

In the following, embodiments of the present invention will be described with reference to the accompanying drawings. In each drawing, the same reference numeral is assigned to the same member, and a duplicate explanation may be omitted.

First Embodiment

[Configuration of Liquid Droplet Forming Apparatus]

At first, a liquid droplet forming apparatus according to the first embodiment will be described. FIG. 1 is a diagram schematically depicting an example of the liquid droplet forming apparatus according to the first embodiment. Referring to FIG. 1, the liquid droplet forming apparatus 10 includes a liquid chamber 11, a membrane 12, a piezoelectric element 13, and a particle state detection unit 14. FIG. 1 schematically illustrates a state where particle suspension liquid 300 including precipitated particles 350 is retained in the liquid chamber 11.

In the embodiment, for the sake of simplicity, a side of the liquid chamber 11 will be referred to an upper side, and a side of the piezo electric element 13 will be referred to as a lower side. Moreover, a face of each member on the side of the liquid chamber 11 will be referred to as an upper face, and a face of each member on the side of the piezo electric element 13 will be referred to as a lower face. Furthermore, planar view will be referred to as viewing an object from a normal direction of an upper face of the membrane 12. Planar shape will be referred to as a shape of an object viewed from the normal direction of the upper face of the membrane 12.

In the liquid droplet forming apparatus 10, the liquid chamber 11 is a liquid retention unit for retaining particle suspension liquid 300 suspending precipitated particles 350 (precipitated particles 350 are dispersed), and may be formed of metal, silicon, ceramic or the like. The liquid chamber 11 has an atmospheric air open unit 111 for opening the inside of the liquid chamber 11 to the atmospheric air in an upper part of the liquid chamber 11. The liquid chamber 11 is configured so that a bubble mixed into the particle suspension liquid 300 can be ejected from the atmospheric air open unit 111.

The membrane 12 is a membrane member fixed to the lower end of the liquid chamber 11. Almost at a center of the membrane 12, a nozzle 121 that is a through hole is formed. The particle suspension liquid 300 retained in the liquid chamber 11 is discharged as a liquid droplet from the nozzle 121 by vibration of the membrane 12. The planar shape of the membrane 12 may be, for example, a circle, but may be an ellipse, a quadrangle or the like.

A material of the membrane 12 is not particularly limited. However, when the membrane 12 is too soft, the membrane vibrates easily and the vibration may be difficult to be suppressed promptly when the discharge is not performed. Then, using a material having hardness to some extent is preferable. As a material of the membrane 12, for example, a metallic material, a ceramic material, a high-molecular material having hardness to some extent, or the like may be used.

Especially, upon using cells as the precipitated particle 350, a material having a low adherability to a cell or protein is preferable. The adherability to a cell is said to depend on a contact angle. When hydrophilicity or hydrophobicity of the material is high, the adherebility of the material is low. As a material having high hydrophilicity, various metallic material, or a ceramic material (metal oxide) may be used. As a material having high hydrophobicity, a fluorine resin or the like may be used.

The other examples of such materials include stainless steel, nickel, aluminum or the like, and silicon dioxide, alumina, zirconia or the like. Other than these materials, cell adhesiveness can be reduced by coating a surface of a material. For example, the surface of the material can be coated with the metal or the metallic oxide material, described as above, or can be coated with synthesized phospholipid polymer representing a cell membrane (e.g. Lipidure by NOF Corporation).

The nozzle 121 is preferably formed as a through hole having actually a shape of an exact circle almost at a center of the membrane 12. In this case, a diameter of the nozzle 121 is not particularly limited, but preferably greater than or equal to twice the size of the precipitated particle 350 in order to prevent the precipitated particle 350 from getting stuck in the nozzle 121. Specifically, because sizes of animal cells, especially human cells are generally about 5 µm to 50 µm, the diameter of the nozzle 121 is preferably 10 µm to 100 µm or more according to cells to be used.

On the other hand, when a liquid droplet is too great, achievement of the purpose to form minuscule droplets becomes difficult. Therefore, the diameter of the nozzle 121 is preferably less than or equal to 200 µm. That is, in the liquid droplet forming apparatus 10 according to the embodiment, the diameter of the nozzle 121 most often falls within a range of 10 µm to 200 µm.

The piezoelectric element 13 is formed on the lower face of the membrane 12. A shape of the piezoelectric element 13 can be designed for the shape of the membrane 12. For example, when the planar shape of the membrane 12 is a circle, the piezoelectric element 13 having a shape of a planar shape of a ring is preferably arranged around the nozzle 121.

The piezoelectric element 13 has, for example, a structure in which electrodes for applying an electric voltage are arranged on an upper face and a lower face of a piezoelectric material. When an electric voltage is applied to the upper and lower electrodes of the piezoelectric element 13, a compression stress is applied in a lateral direction of the plane of paper, and thereby the membrane 12 vibrates in a vertical direction of the plane of paper. As the piezoelectric material, for example, lead zirconate titanate may be used. Other than the lead zirconate titanate, various piezoelectric material may be used such as bismuth iron oxide, metal niobate, barium titanate, or a material obtained by adding metal or other oxide to these materials.

However, the vibration means for vibrating the membrane 12 is not limited to the piezoelectric element 13. For example, adhering on the membrane 12 a material having a different linear expansion coefficient from the membrane 12, by heating the membrane 12 can be caused to vibrate by using the difference of the linear expansion coefficient. On this occasion, the membrane 12 preferably has a configuration where a heater is formed in a material having different linear expansion coefficient, and the heater is heated by conducting, and thereby the membrane 12 vibrates.

The particle state detection unit 14 is arranged above the liquid chamber 11, and detects from a side of the liquid chamber 11 a particle state of the precipitated particles 350 in the particle suspension liquid 300 and around the nozzle 121 by using an optical method.

Here, the "around the nozzle 121" refers to at least a part of a region of the entire nozzle 121 and the upper face of the membrane 12 that contacts the nozzle 121. However, the size of the region of the upper face of the membrane 12 does not matter. That is, according to the design of the optical system, the particle state in a quite narrow region of the entire nozzle 121 and the upper face of the membrane 12 that contacts the nozzle 121 can be acquired, and the particle state of almost whole region of the entire nozzle 121 and the upper face of the membrane 12 that contacts the nozzle 121 can be acquired.

A range around the nozzle that detects a particle state is preferably a region determined experimentally. For example, a typical example of the present invention includes a configuration in which a liquid droplet with a liquid droplet size of 200 pl is discharged tom a nozzle with a nozzle diameter of 80 µm and a thickness of membrane of 20 µm. In this case, a volume of liquid retained in a nozzle part is 100 pl, and the size of the discharged liquid drop includes liquid from around the nozzle part. As the range that can include a particle, a range within 100 µm from a center of the nozzle is preferably the "around the nozzle". This range is most preferably determined optimally for the configuration of the ink jet head or the size of the discharged liquid drop, and preferably obtained by experiment.

Figure 4A:
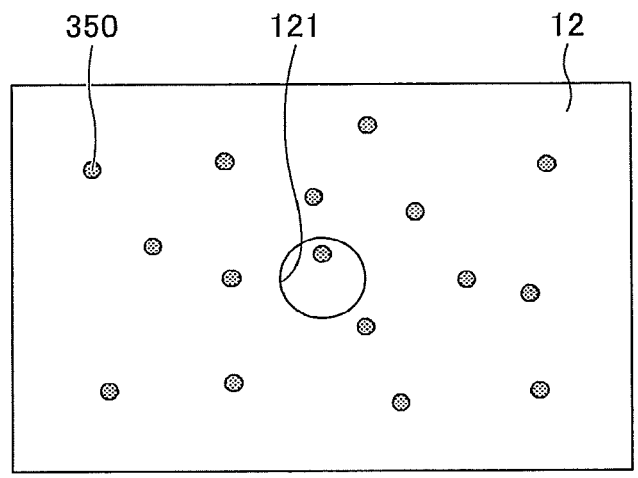
FIGS. 4A and 4B are diagrams depicting an example of a state of particles around a nozzle observed by a particle state detection unit.
Figure 4B:
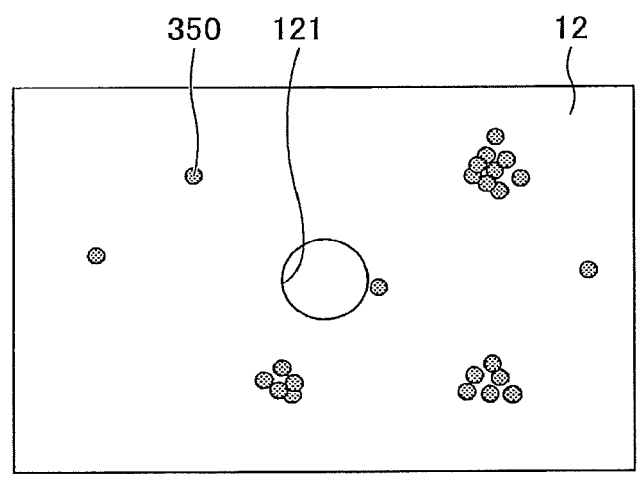
Figure 5:
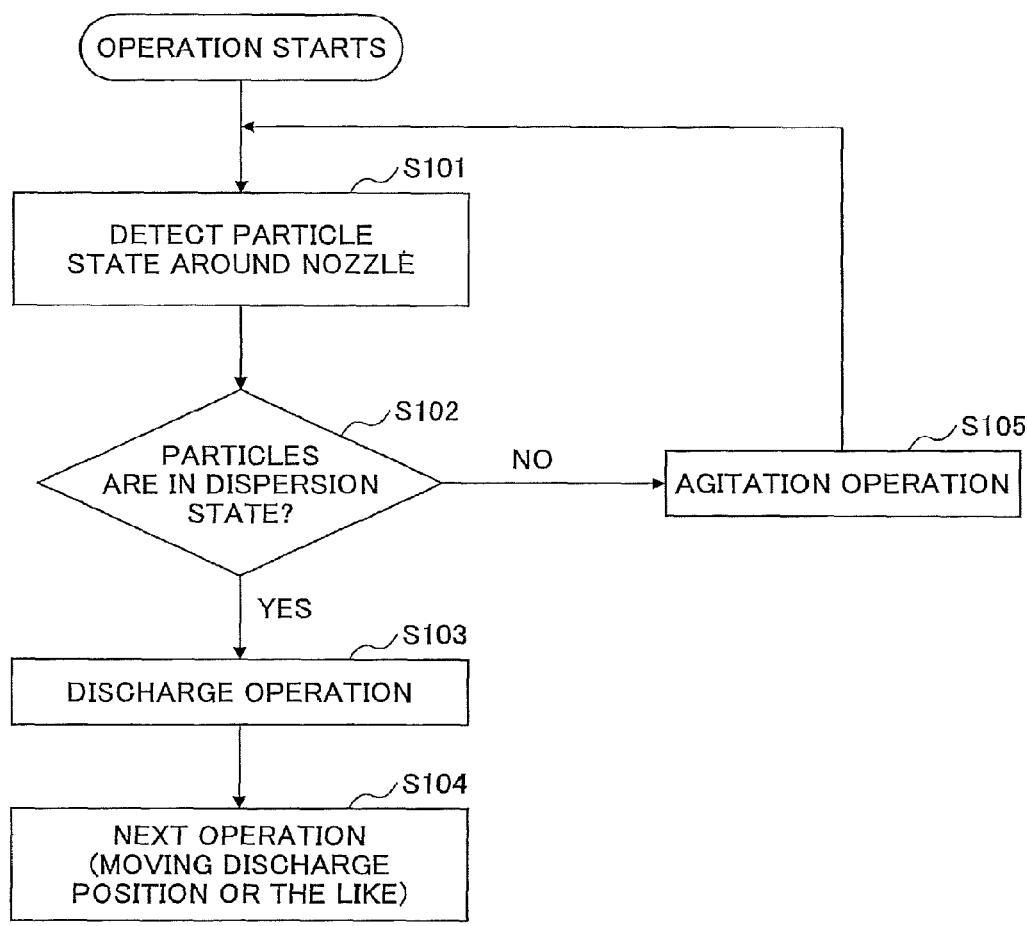
FIG. 5 is a flowchart depicting an example of an operation of a liquid droplet forming apparatus according to the first embodiment.

Moreover, the particle state includes at least presence or absence of particles, a number of particles, and density of particles. Moreover, detecting the particle state means, as illustrated in FIG. 4 that will be described later, optically observing (acquiring optical information) difference in particle states. That is, the particle state detection unit 14 is a means for detecting (observing) at lease one of presence or difference of particles, a number of particles and a density of particles, and two or more of them may be detected simultaneously.

The particle state detection unit 14 includes an imaging lens 141, and a two-dimensional imaging element 142. Dashed lines in FIG. 1 schematically illustrate optical paths in the particle state detection unit 14. As the two-dimensional imaging element 142, for example, a CCD (Charge Coupled Device), a CMOS (Complementary Metal Oxide Semiconductor), or the like may be used. The two-dimensional imaging element 142 is a representative example of a light receiving unit according to the present invention. The detection method of the particle state detection unit 14 will be specifically described later.

As the precipitated particles 350, metallic fine particles, inorganic fine particles, or cells, in particular human cells or the like are assumed. In the embodiment, because the state of the particle is detected by the particle state detection unit 14 using the optical method, a particle size of the object is preferably 1 µm or more.

When a cell solution in which cells, in particular, are suspended is used as the particle suspension liquid 300, a variety of changes in the state of particles may occur, such as adhesion to base material of cell, division of cell, death of cell, aggregation among cells, etc. Therefore, monitoring the state of particles in the liquid chamber is important, and suitable as a use of the apparatus of the present invention. In the specification, embodiments where human cells are used as particles will be described mainly, but the use is not limited to cells.

When a cell suspension liquid in which cells, especially human cells, are dispersed is used as the particle suspension liquid 300, water having a high degree of affinity for cells is used for a main component of the cell suspension liquid. Furthermore, the solution preferably includes salt for controlling osmotic pressure with cells, and pH adjuster for adjusting pH. More preferably, as the cell suspension liquid, Tris buffer solution in which pH is controlled or PBS solution in which metallic salt of Ca, K, Na or the like is added equivalently with culture solution may be used.

Alternatively, as the cell suspension liquid, a culture medium for cell culture normally used in the technical field can be used without restriction in particular. For example, according to types of cells to be used, a basal medium described in "Technology of tissue culture, 3rd edition" (Ed by Japanese Tissue Culture Association, Asakura Publishing Co., Ltd. June 1996), p. 581, such as a MEM culture medium, a BME culture medium, a DME culture medium, an αMEM culture medium, an IMDM culture medium, an ES culture medium, a DM-160 culture medium, a Fisher culture medium, an F12 culture medium, a WE culture medium, or a RPMI 1640 culture medium can be used.

Furthermore, to a basal medium, serum (Fetal bovine serum or the like), various growth factors, an antibiotic substance, an amino acid or the like may be added. Moreover, a commercial serum-free culture medium, such as Gibco serum-free culcure medium (Invitrogen Corporation), may be used.

The liquid droplet forming apparatus 10 is configured so as to be connectable to a drive device 500. The drive device 500 includes a control unit 510 and a drive unit 520. The control unit 510, for example, acquires a detection result of the particle state detection unit 14, and can select a drive waveform for driving the piezoelectric element 13 based on the detection result. The drive unit 520 converts the drive waveform selected by the control unit 510 into a signal that can drive the piezoelectric element 13, and thereby drives the piezoelectric element 13.

The control unit 510 may have a configuration, for example, including a CPU (Central Processing Unit), a ROM (Read-Only Memory), a RAM (Random Access Memory), a main memory and the like. In this case, respective functions of the control unit 510 are enabled by a program stored in the ROM or the like read onto the main memory and executed by the CPU. However, a part of or the entire control unit 510 may be enabled only by hardware. Moreover, the control unit 510 may be configured physically with a plurality of devices or the like.

In this way, the drive device 500 can selectively (e.g. alternately) give, to the piezoelectric element 13, a discharge waveform for causing the membrane 12 to vibrate to form liquid droplets and an agitation waveform for causing the membrane 12 to vibrate in a range of not forming liquid droplets, based on the detection result of the particle state detection unit 14. For example, the drive device 500 performs a discharge operation when determining that particles are in a dispersed state based on the detection result of the particle state detection unit 14, and performs an agitation operation when determining that the particles are in an aggregation state.

That is, the drive device 500 applies a discharge waveform to the piezoelectric element 13, controls a vibration state of the membrane 12, and thereby discharges the particle suspension liquid 300 retained in the liquid chamber 11 from the nozzle 121 as liquid droplets. Moreover, the drive device 500 applies an agitation waveform to the piezoelectric element 13, controls a vibration state of the membrane 12, and thereby agitates the particle suspension liquid 300 retained in the liquid chamber 11. When the particle suspension liquid is agitated, liquid droplets are not discharged from the nozzle 121.

However, the configuration where the liquid droplet forming apparatus 10 is connectable to the drive device 500 is an example, and the present invention is not limited to this. For example, the detection result of the particle state detection unit 14 may be displayed on a display device (a liquid crystal display device or the like), and a user of the liquid droplet forming apparatus 10 may view the display device and determine whether the particles are in a particle state suitable for discharging. In this case, the apparatus may have a configuration where the user can switch manually between the discharge waveform and the agitation waveform.

[Liquid Droplet Formation Process of Liquid Droplet Forming Apparatus]

Figure 2A:
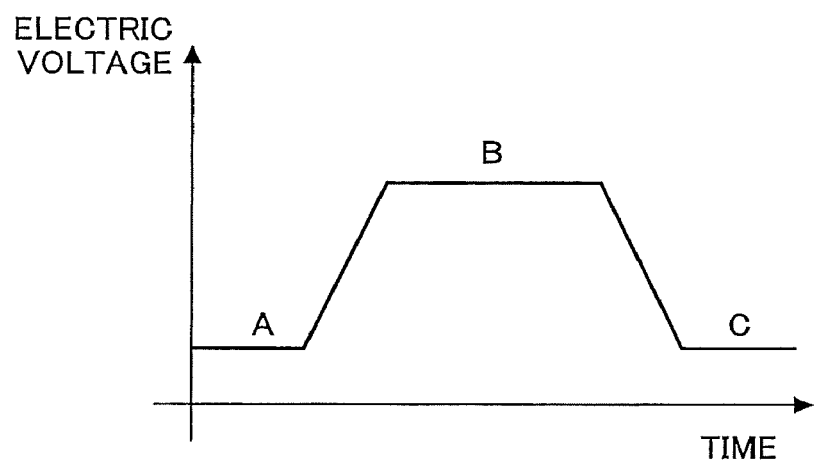
FIGS. 2A and 2B are diagrams depicting an example of an electric voltage applied to upper and lower electrodes of a piezoelectric element.
Figure 2B:
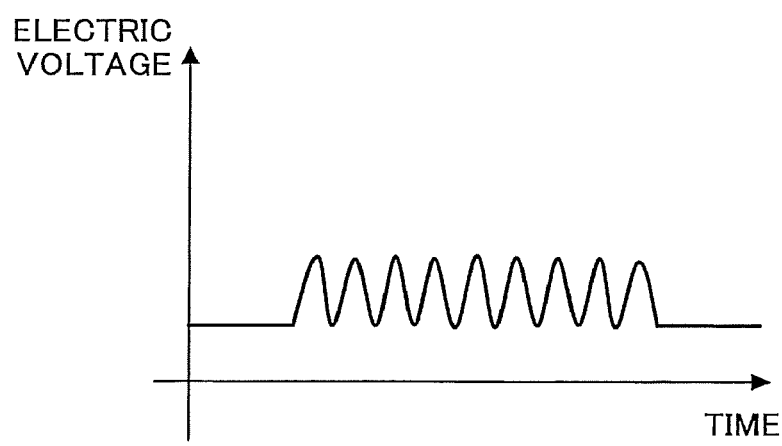
Figure 3A:
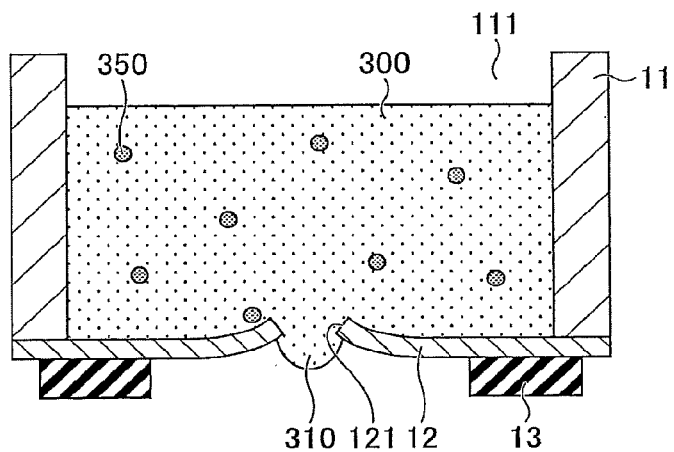
FIGS. 3A to 3C are diagrams depicting an example of a process of forming a liquid droplet.
Figure 3B:
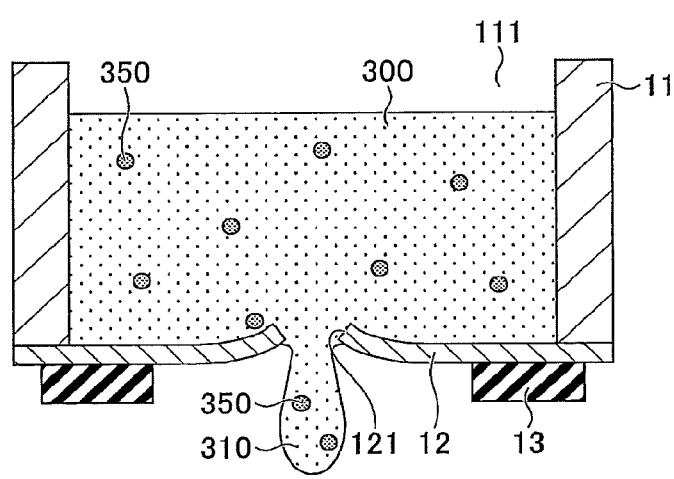
Figure 3C:
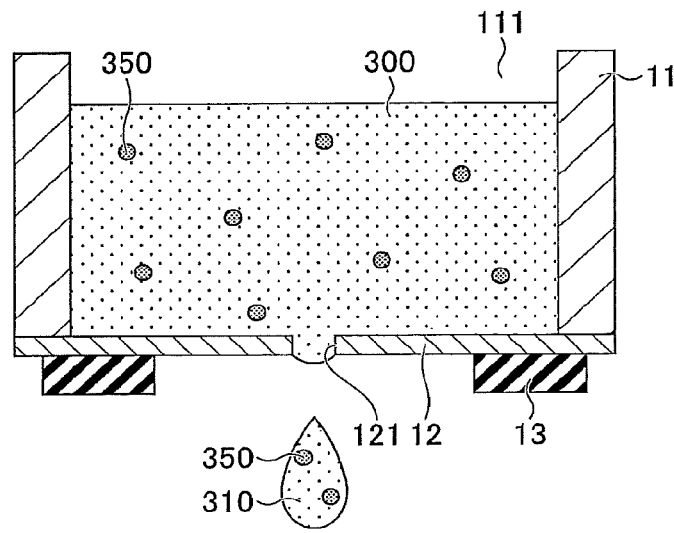

Next, a process of forming a liquid droplet by the liquid droplet forming apparatus according to the first embodiment will be described. FIGS. 2A and 2B are diagrams depicting an example of electric voltages applied to the upper and lower electrodes of the piezoelectric element. FIG. 2A illustrates a discharge waveform that is a drive waveform for forming a liquid droplet, and FIG. 2B illustrates an agitation waveform that is a drive waveform for agitating particles without performing discharging. FIGS. 3A to 3C are diagrams depicting an example of a process where a liquid droplet is formed, and illustrate a part of the liquid droplet forming apparatus 10.

At first, the discharge operation will be described. When a pulsed electric voltage illustrated in FIG. 2A is applied to the upper and lower electrodes of the piezoelectric element 13 of the liquid droplet forming apparatus 10, a liquid droplet is formed as illustrated in FIGS. 3A to 3C. At first, in a timing of A in FIG. 2A, as illustrated in FIG. 3A, according to a rapid deformation of the membrane 12, a high pressure is generated between the particle suspension liquid 300 retained in the liquid chamber 11 and the membrane 12. Then, by the pressure, a liquid droplet 310 is pushed out from the nozzle 121.

Next, in a timing of B in FIG. 2A, as illustrated in FIG. 3B, while the pressure is dissipated upward, the pushing out of liquid from the nozzle 121 continues and the liquid droplet 310 grows. Finally, in a timing of C in FIG. 2A, as illustrated in FIG. 3C, when the membrane 12 returns to the original state, a liquid pressure around an interface between the particle suspension liquid 300 and the membrane 12 decreases, and a liquid droplet 310 including the precipitated particle 350 is formed.

Next, the agitation operation will be described. As an electric voltage applied to the piezoelectric element 13, a plurality of pulses, not so strong as to discharge a liquid droplet, are input, as illustrated in FIG. 2B. By the application of the electric voltage, the membrane 12 vibrates in a vertical direction, and a flow occurs in the particle suspension liquid 300 retained in the liquid chamber 11. Therefore, redispersion of the aggregated precipitated particles 350 can be facilitated.

In the liquid droplet forming apparatus 10, an air bubble may be mixed into the particle suspension liquid 300 in the liquid chamber 11. However, because the liquid droplet forming apparatus 10 according to the embodiment is provided with the atmosphere air open unit 111 in an upper part of the liquid chamber 11, the air bubbles mixed into the particle suspension liquid 300 can be ejected to the air through the atmosphere air open unit 111. Therefore, liquid droplets 310 can be formed continuously and stably without discarding a great amount of liquid in order to eject air bubbles.

That is, when an air bubble is mixed near the nozzle 121, or a great number of air bubbles are mixed on the membrane 12, the discharge state is affected. Then, in order to perform stable formation of liquid droplets for a long time, the mixed air bubbles are required to be ejected. Normally, the air bubbles mixed on the membrane 12 move upward naturally or according to vibration of the membrane 12. Because the atmosphere air open unit 111 is arranged in the liquid chamber 11, the mixed air bubbles can be ejected from the atmosphere air open unit 111.

In addition, in a timing of not forming liquid droplets, the membrane 12 can be vibrated in a range of not forming liquid droplets: thereby the air bubbles are moved actively to the upper part of the liquid chamber 11.

In this way, because the liquid chamber 11 is provided with the atmosphere air open unit 111, the liquid droplet forming apparatus 10 according to the first embodiment can eject air bubbles mixed into the liquid chamber 11 to the air through the atmosphere air open unit 111. Therefore, different from an inkjet head having a normal pressurized liquid chamber, an occurrence of discharge failure can be prevented even when air bubbles are mixed into the liquid chamber 11, and liquid droplets 310 can be formed continuously and stably.

[Particle State Detection Unit]

Next, the liquid droplet forming apparatus according to the first embodiment will be described. The liquid droplet forming apparatus 10 can discharge the particle suspension liquid 300 in the liquid chamber 11 in the form of liquid droplets by vibration of the membrane 12 in which the nozzle 121 is formed. In the liquid droplet forming apparatus 10, because a cavity is not formed, different from inkjet printers, a particle state of the precipitated particles 350 around the nozzle 121 can be easily observed and detected from above the liquid chamber 11.

Therefore, compared with a conventional apparatus in which a liquid state or a particle state is observed from a side, a degree of freedom of arranging the droplet arrival object unit and the liquid droplet forming apparatus can be made higher. In other words, in a state where a distance between the nozzle 121 and the droplet arrival object unit is kept short, the particle state around the nozzle 121 can be detected.

The particle state detection unit 14 will be described in more detail as follows. FIGS. 4A and 4B are diagrams depicting examples of particle state around the nozzle 121 observed by the particle state detection unit 14. In FIG. 4A, precipitated particles 350 are dispersed uniformly, and are in a state suitable for forming liquid droplets. In contrast, in FIG. 4B, a part of precipitated particles 350 form an aggregate, and are in a state not suitable for forming liquid droplets.

In addition, as a state which is not suitable for forming liquid droplets, different from FIG. 4B, a case where great number of precipitated particles 350 are present can be considered. Also at this time, by focusing on the membrane 12, precipitated particles 350 can be detected. In this way, because the liquid droplet forming apparatus 10 is provided with the particle state detection unit 14, difference in particle states can be observed, and the particle state can be determined whether to be suitable for discharging by the user's view or by image processing automatically.

FIG. 5 is a flowchart depicting an example of an operation of the liquid droplet forming apparatus 10 according to the first embodiment. At first, the particle state detection unit 14 receives scattering light from precipitated particles 350 around the nozzle 121, and sends a two-dimensional image obtained from the received scattering light to the drive device 500 (step S101).

Next, the control unit 510 of the drive device 500 determines whether the particle state of the precipitated particles 350 is a dispersed state based on the two-dimensional image obtained from the precipitated particles 350 (step S102). The control unit 510 can determine whether the particle state of the precipitated particles 350 is a dispersed state or an aggregation state, for example, by extracting a region of particles by threshold processing, measuring particle sizes, and detecting whether the particle sizes are greater than prescribed value, for the two-dimensional image acquired from the particle state detection unit 14, illustrated in FIG. 4A or 4B.

Alternatively, a general method for calculating a degree of distribution concentration can also be applied. For example, the particle state of the precipitated particles 350 can be determined whether to be a dispersed state or an aggregation state by dividing the acquired two-dimensional image into sections with a proper size, counting a number of particles included in the respective sections, and obtaining an index of dispersion that is obtained by dividing a variance of the number of particles by an average.

When the control unit 510 determines that the particle state of the precipitated particles 350 is the dispersed state (step S102: YES), the process proceeds to step S103. The control unit 510 outputs the discharge waveform to the drive unit 520 (step S103). The drive unit 520 drives the piezoelectric element 13 based on the discharge waveform from the control unit 510, and performs the discharge operation.

After the discharge operation ends, a next operation (moving the discharge position or the like) is performed (step S104).

On the other hand, when the control unit 510 determines that the particle state of the precipitated particles 350 is not the dispersed state (aggregation state) (step S102: NO), the process proceeds to step S105. The control unit 510 outputs the agitation waveform to the drive unit 520 (step S105). The drive unit 520 drives the piezoelectric element 13 based on the agitation waveform from the control unit 510, and performs the agitation operation. After the agitation operation ends, the process returns to S101, and the same process described as above is repeated.

In this way, in the liquid droplet forming apparatus 10, by the particle state detection unit 14, the particle state around the nozzle 121 (e.g. number of particles) can be detected. Then, by determining whether the precipitated particles 350 is in the dispersed state or in the aggregation state using the information, an electric voltage waveform applied to the piezoelectric element 13 can be switched between the discharge waveform and the agitation waveform. Therefore, a liquid droplet can be prevented from being discharged in a state where the precipitated particles 350 are in the aggregated state or the precipitated state, and the number of precipitated particles 350 included in a liquid droplet or the discharging state can be stabilized.

Figure 6:
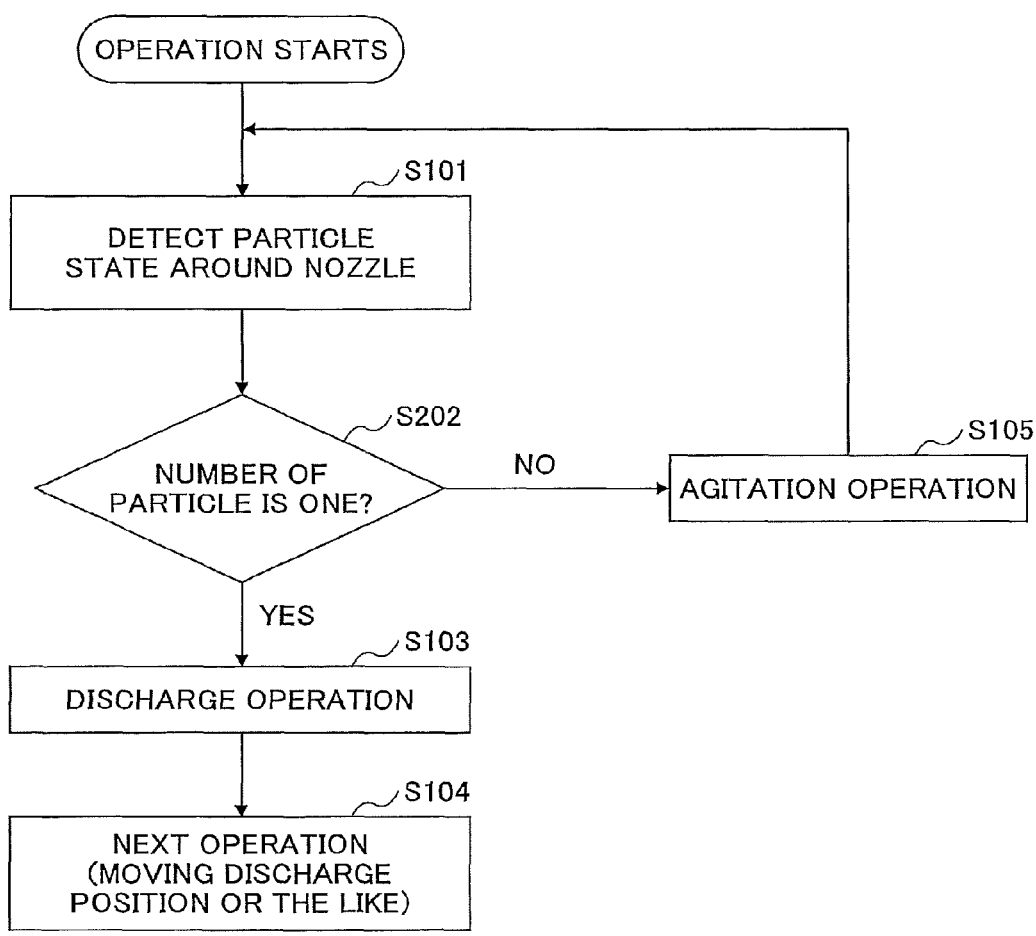
FIG. 6 is a flowchart depicting another example of an operation of the liquid droplet forming apparatus according to the first embodiment.

By using the liquid droplet forming apparatus 10, as illustrated in FIG. 6, a precipitated particle 350 can be encapsulated in a liquid droplet and discharged. FIG. 6 is a flowchart depicting another example of the operation of the liquid droplet forming apparatus according to the first embodiment. At first, the particle state detection unit 14 detects a particle state of the precipitated particles 350 around the nozzle 121, and sends a two-dimensional image that is a detection result to the drive device 500 (step S101).

Next, the control unit 510 of the drive device 500 determines whether a number of precipitated particles 350 around the nozzle 121 is one, based on the two-dimensional image obtained from the precipitated particles 350 (step S202). The control unit 510 cuts out, for example, an image only around the nozzle 121 from the two-dimensional image, illustrated in FIG. 4A or 4B, acquired from the particle state detection unit 14, and counts a number of only the precipitated particles 350 around the nozzle 121. On this occasion, a method of extracting only the precipitated particles 350 having an edge contrast greater than or equal to a predetermined threshold value, and counting can be employed.

When the control unit 510 determines that the number of precipitated particles 510 is one (step S202: YES), the process proceeds to step S103. The control unit 510 outputs the discharge waveform to the drive unit 520 (step S103). The drive unit 520 drives the piezoelectric element 13 based on the discharge waveform from the control unit 510, and performs the discharge operation. After the discharge operation ends, a next operation (moving the discharge position or the like) is performed (step S104).

On the other hand, when the control unit 510 determines that the number of precipitated particles 350 is not one (step S202: NO), the process proceeds to step S105. The control unit 510 outputs the agitation waveform to the drive unit 520 (step S105). The drive unit 520 drives the piezoelectric element 13 based on the agitation waveform from the control unit 510, and performs the agitation operation. After the agitation operation ends, the process returns to S101, and the same process described as above is repeated.

In this way, in the liquid droplet forming apparatus 10, because the liquid chamber does not form a cavity, the particle state detection unit 14 can be arranged on the side of the liquid chamber 11. Therefore, in a state where a distance between the nozzle 121 and the droplet arrival object unit is kept short, the particle state around the nozzle 121 can be detected.

Moreover, because one precipitated particle 350 can be encapsulated into a liquid droplet and discharged, when the precipitated particle 350 is a cell, for example, in each of a lot of wells one cell can be discharged, and a gene or a gene expression state of each cell can be analyzed.

That is, normally, numbers of particles included in a liquid droplet discharged from particle suspension liquid are distributed according to a Poisson distribution. On the other hand, when a predetermined number of particles can be discharged at a predetermined position with higher controllability, an unconventional accurate liquid droplet forming apparatus is enabled.

Especially, in research using human cells, a single cell gene analysis and gene expression analysis for grasping individual characteristics of each cell is desired to be realized, compared with the conventional gene analysis or gene expression analysis for many cells. For this purpose, a simple device for dispensing each cell into a predetermined position is necessary.

Because the liquid droplet forming apparatus 10 can detect a particle state around the nozzle 121 by the particle state detection unit 14, the membrane 12 can be caused to vibrate based on a detection result. For example, when a number of particles is appropriate, the discharge operation is performed, when the number of particles is inappropriate, the agitation operation is performed, and thereby particles of a predetermined number or within a predetermined range can be discharged stably. Therefore, a distribution of the numbers of particles becomes sharper than a Poisson distribution, and in particular, a particle can be encapsulated in a liquid droplet and discharged.

Moreover, in a conventional inkjet head in which a cavity is pressurized to form a liquid droplet, when an air bubble is mixed into the cavity, the pressure of the cavity is reduced by the air bubble, the cavity cannot be pressurized, and discharge becomes impossible. In contrast, in the liquid droplet forming apparatus 10, because only the space around the nozzle 121 is pressurized by deformation of the membrane 12, even if an air bubble is mixed, the air bubble is hard to affect.

When an air bubble is mixed around the nozzle 121 or a lot of bubbles are mixed on the membrane 12, the discharge state is influenced. However, because the air bubbles mixed on the membrane 12 move upward naturally or according to vibration of the membrane 12, the discharge state recovers in a short period of time. Therefore, in the liquid droplet forming apparatus 10, even for a cell suspension liquid having high surface tension, liquid droplet formation can be performed stably.

In an apparatus that discharges minuscule liquid droplets, great separation between a discharge part, i.e. the nozzle, and a droplet arrival object unit is not desirable, because the liquid droplet may be decelerated in between and an accurate discharge in a desired direction may not be possible. Therefore, in apparatuses, which discharge minuscule liquid droplets such as inkjets, a distance between the nozzle and the droplet arrival object unit is generally a few mm or less, more preferably 1 mm or less.

However, in any of the above-described techniques, a liquid droplet is observed from a side with respect to the discharge direction. At this time, there is a problem that because a large detection unit including a lens or a camera is arranged on the side, the droplet arrival object unit may interfere with the detection unit, and a distance between the nozzle and the droplet arrival object unit may be difficult to be kept short.

According to the embodiment, a liquid droplet forming apparatus that can detect a state of a particle around the nozzle in the state where the distance between the nozzle and the droplet arrival object unit is kept short can be provided.

First Variation of First Embodiment

In a first variation of the first embodiment, an example of a liquid droplet forming apparatus that can acquire a fluorescent image from a precipitated particle will be described. In the first variation of the first embodiment, an explanation for the same component as that in the embodiment, which has already been explained, may be omitted.

Figure 7:
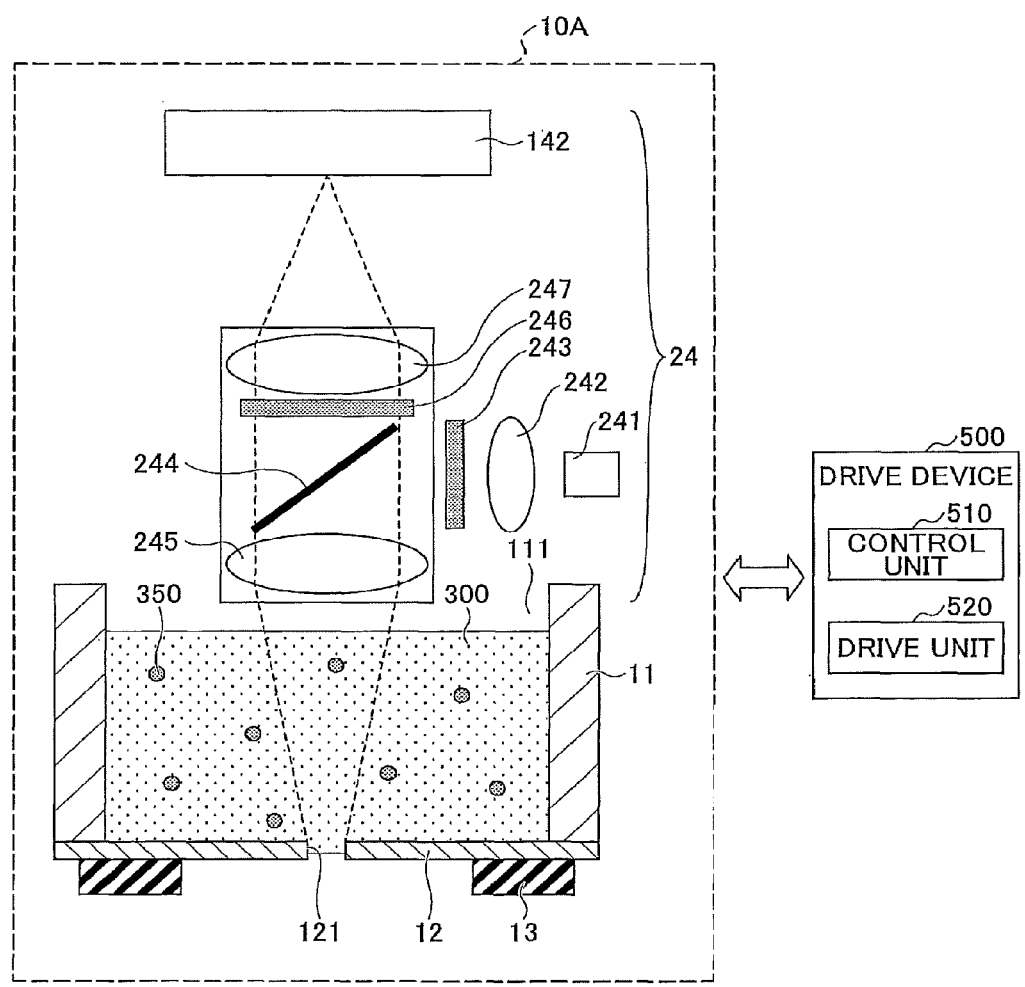
FIG. 7 is a diagram schematically depicting an example of a liquid droplet forming apparatus according to a first variation of the first embodiment.

FIG. 7 is a diagram schematically depicting an example of a liquid droplet forming apparatus according to the first variation of the first embodiment. Referring to FIG. 7, the liquid droplet forming apparatus 10A is different from the liquid droplet forming apparatus 10 (See FIG. 1), in that the particle state detection unit 14 is replaced by a particle state detection unit 24.

The particle state detection unit 24 includes a light source 241, a lens 242, an excitation filter 243, a dichroic mirror 244, an imaging lens 245, a fluorescent filter 246, an imaging lens 247, and a two-dimensional imaging element 142.

In the liquid droplet forming apparatus 10A, light from the light source 241 passes through the lens 242, via the excitation filter 243 that transmits only light with wavelength suitable for performing optical excitation for the precipitated particle 350 (excitation light), and enters the dichroic mirror 244. Then, an optical path of the excitation light is converted by the dichroic mirror 244, the excitation light is condensed by the imaging lens 245, and the particle suspension liquid 300 is irradiated with the condensed light.

In the particle suspension liquid 300, as the precipitated particles 350, fluorescent particles that yield fluorescence by excitation light from the light source 241 are dispersed. The fluorescent particles yield fluorescence by the excitation light from the light source 241. The fluorescence from the fluorescent particles is collected by the imaging lens 245, and enters the dichroic mirror 244. Then, the fluorescence passes through the dichroic mirror 244. After light other than the fluorescence is cut by the fluorescent filter 246, the fluorescence is focused on the two-dimensional imaging element 142 by the imaging lens 247.

As the fluorescent particle, for example, an inorganic fine particle preliminarily stained with fluorescent dye, an organic polymer particle, or the like can be used. Moreover, a fluorescently stained cell, a cell that can express fluorescent protein or the like can be used.

In this way, in the first variation of the first embodiment, as the precipitated particle 350, a fluorescent particle is used. Therefore, in addition to the effect of the first embodiment, the following effect is achieved. That is, in the liquid droplet forming apparatus 10A, by making a specific particle, a state of which is desired to be obtained, a fluorescent particle, the particle state of the specific particle becomes detectable with high sensitivity and an influence of contamination can be excluded.

Furthermore, as an application, two or more fluorescent wavelengths and excitation wavelengths can be used. On this occasion, as the excitation filter 243 and the fluorescent filter 246, filters that transmit a plurality of wavelengths can be used. As the two-dimensional imaging element 142, a sensor that can acquire a plurality of wavelengths, e.g. a full color CCD, can be used.

Therefore, for example, in a state where a plurality of kinds of cells are mixed, only one cell of a specific cell can be discharged. Moreover, in some dyeing method for cells, a fluorescent wavelength for a live cell can be made different from a fluorescent wavelength for a dead cell, and the live cell can be discharged while the dead cell is not discharged.

As the light source 241, a mercury lamp, LED (light-emitting diode), or the like, which is generally used in a fluorescent observation, can be used. When LED is used as the light source 241, the excitation filter 243 can be omitted. Moreover, by using LEDs of a plurality of colors, a plurality of excitation wavelengths can be provided. On this occasion, by turning on the LEDs serially in synchronization with an imaging timing of the two-dimensional imaging element 142, an image for the plurality of excitation wavelengths can be acquired.

Second Variation of First Embodiment

In a second variation of the first embodiment, an example of a liquid droplet forming apparatus in which a light source or the like is arranged on an opposite side of the droplet arrival object unit to a droplet arrival side will be described. In the second variation of the first embodiment, an explanation for the same component as that in the embodiment, which has already been explained, may be omitted.

Figure 8:
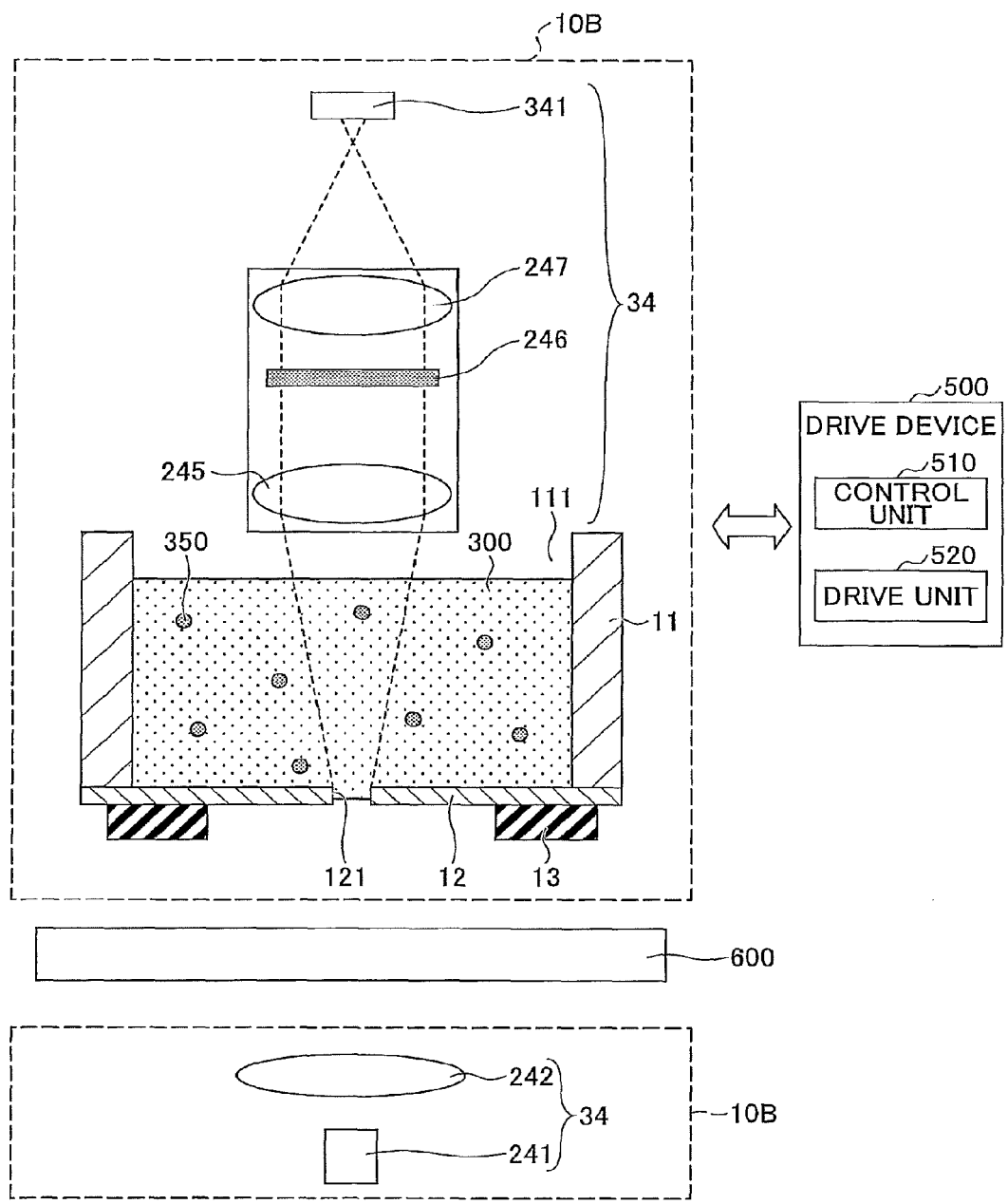
FIG. 8 is a diagram schematically depicting an example of a liquid droplet forming apparatus according to a second variation of the first embodiment.

FIG. 8 is a diagram schematically depicting an example of a liquid droplet forming apparatus according to the second variation of the first embodiment. Referring to FIG. 8, the liquid droplet forming apparatus 10B is different from the liquid droplet forming apparatus 10A (See FIG. 7) in that the particle state detection unit 24 is replaced by a particle state detection unit 34. The precipitated particle 350 is a florescent particle in the same way as the first variation of the first embodiment.

The particle state detection unit 34 includes a light source 241, a lens 242, an imaging lens 245, a fluorescent filter 246, an imaging lens 247 and a light receiving element 341. The light receiving element 341 is a light receiving element of one pixel. For the light receiving element 341, for example, a photodiode, an avalanche photodiode, a photomultiplier tube or the like can be used. The light receiving element 341 is a representative example of a light receiving unit according to the present invention.

In the first embodiment and the first variation of the first embodiment, a two-dimensional imaging element 142 is used. However, there is a problem that a frame rate of the two-dimensional imaging element is generally less than or equal to 100 frames/second, which is slow with respect to a speed that a liquid droplet can be formed, and moreover, the two-dimensional image processing takes time. In order to discharge liquid droplets faster, the process of the particle state detection unit 34 is preferably simpler. Then, in the present embodiment, instead of the two-dimensional imaging element, the light receiving element 341 that is a photodiode or the like is used. The particle state detection unit 34 detects the particle state of the precipitated particle 350 around the nozzle 121 based on an amount of light that the light receiving element 341 receives.

In the liquid droplet forming apparatus 10B, the light source 241 and the lens 242 are arranged on an opposite side of the droplet arrival object unit 600 to a droplet arrival side. Therefore, in the liquid droplet forming apparatus 10B, for the droplet arrival object unit 600, a material having light permeability is required to be used.

In the liquid droplet forming apparatus 10B, light emitted from the light source 241 passes through the lens 242 and the droplet arrival object unit 600, and the membrane 12 is irradiated with the light. Because the membrane 12 is generally formed with a material that does not have light permeability, most of light is blocked by the membrane 12, and the particle suspension liquid 300 is irradiated only with slight light passing through the nozzle 121.

The precipitated particles 350 (fluorescent particles) existing around the nozzle 121 emit fluorescence by excitation light from the light source 241, and the fluorescence from the fluorescent particles is collected by the imaging lens 245 and light other than the fluorescence is cut by the fluorescent filter 246. Afterwards, the fluorescence is focused on the light receiving element 341 by the imaging lens 247.

In the control unit 510, for the signal intensity obtained by the light receiving element 341, a first threshold that separates a case where a fluorescent particle does not exist from a case where only one fluorescent particle exists, and a second threshold that separates the case where only one fluorescent particle exists from a case where two fluorescent particles exist are set in advance. Therefore, by setting two appropriate thresholds, the control unit 510 can determine that only one fluorescent particle exists around the nozzle 121 when the signal intensity obtained by the light receiving element 341 indicates a value between the first threshold and the second threshold.

In this way, in the second variation of the first embodiment 2, instead of the two-dimensional imaging element 142, the light receiving element 341 such as a photodiode or the like is used. Therefore, in addition to the effect of the first variation of the first embodiment, the following effect is achieved. That is, in the liquid droplet forming apparatus 10B, the particle state can be detected in shorter time.

Moreover, in the liquid droplet forming apparatus 10B, by the imaging lens 247 that is an imaging optical element, the light receiving element 341 and the nozzle 121 are preferably arranged so that the light receiving element 341 and the nozzle 121 are made conjugate to each other. Therefore, the light receiving element 341 mainly receives only fluorescence from particles positioned in an extremely narrow region around the nozzle 121, and the particle state in the extremely narrow region around the nozzle 121 can be detected exactly.

Third Variation of First Embodiment

In a third variation of the first embodiment, an example of a liquid droplet forming apparatus in which a pinhole is arranged on an incident side of a light receiving element will be described. In the third variation of the first embodiment, an explanation for the same component as that in the embodiment, which has already been explained, may be omitted.

Figure 9:
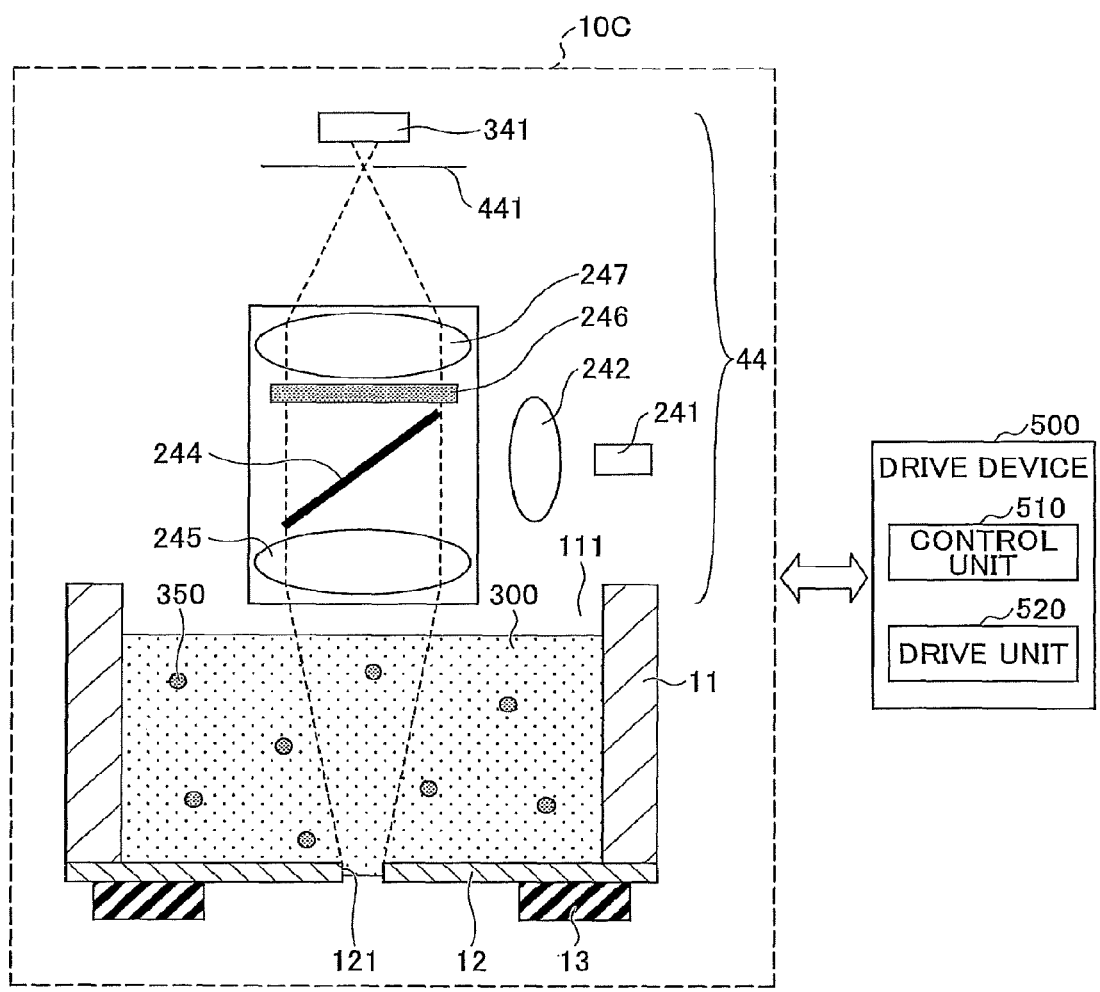
FIG. 9 is a diagram schematically depicting an example of a liquid droplet forming apparatus according to a third variation of the first embodiment.

FIG. 9 is a diagram schematically depicting an example of a liquid droplet forming apparatus according to the third variation of the first embodiment. Referring to FIG. 9, the liquid droplet forming apparatus 10C is different from the liquid droplet forming apparatus 10B (See FIG. 8) in that the particle state detection unit 34 is replaced by a particle state detection unit 44, and the light source 241 and the lens 242 are arranged on the same side of the droplet arrival object unit as the droplet arrival side. The precipitated particle 350 is a florescent particle in the same way as the second variation of the first embodiment.

The particle state detection unit 44 includes a light source 241, a lens 242, an imaging lens 245, a fluorescent filter 246, an imaging lens 247, a pinhole 441 and a light receiving element 341.

In the liquid droplet forming apparatus 100, light (excitation light) from the light source 241 passes through the lens 242, and enters the dichroic mirror 244. Then, an optical path of the excitation light is converted by the dichroic mirror 244, the excitation light is condensed by the imaging lens 245, and the particle suspension liquid 300 is irradiated with the condensed light.

The fluorescent particles yield fluorescence by the excitation light from the light source 241. The fluorescence from the fluorescent particles is collected by the imaging lens 245, and enters the dichroic mirror 244. Then, the fluorescence passes through the dichroic mirror 244. After light other than the fluorescence is cut by the fluorescent filter 246, the fluorescence is focused on the light receiving element 341 by the imaging lens 247.

The pinhole 441 is arranged immediately before the light receiving element 341 on the incident side. By the imaging lens 247 that is a imaging optical element, a hole provided in the pinhole 441 and the nozzle 121 are preferably arranged so that the hole and the nozzle 121 are made conjugate to each other. Therefore, the light receiving element 341 mainly receives only fluorescence from particles positioned in an extremely narrow region around the nozzle 121 via the hole provided in the pinhole 441, and the particle state in the extremely narrow region around the nozzle 121 can be detected exactly.

In this way, in the third variation of the first embodiment, the pinhole 441 is arranged immediately before the light receiving element 341 on the incident side. Therefore, in addition to the effect of the second variation of the first embodiment, the following effect is achieved. That is, by arranging the pinhole 441 immediately before the light receiving element 341 so as to be made conjugate to the nozzle 121, and setting a diameter of the hole of the pinhole 441 to be an optimum value, a particle state in an extremely narrow region around the nozzle 121, which is approximately the same as the range discharged upon forming a liquid droplet, can be detected.

Moreover, in the liquid droplet forming apparatus 10C, because the light source 241 or the like is arranged on the same side of the droplet arrival object unit as the droplet arrival side, a material that does not have light permeability can be used for the droplet arrival object unit. Moreover, when the light source 241 or the like is arranged on an opposite side of the droplet arrival object unit to the droplet arrival side, the light source 241 or the like tends to grow in size. However, in the liquid droplet forming apparatus 10C, the light source 241 or the like can be prevented from growing in size.

Fourth Variation of First Embodiment

In a fourth variation of the first embodiment, an example of a liquid droplet forming apparatus including a plurality of light sources, wavelengths of which are different from each other, will be described. In the fourth variation of the first embodiment, an explanation for the same component as that in the embodiment, which has already been explained, may be omitted.

Figure 10:
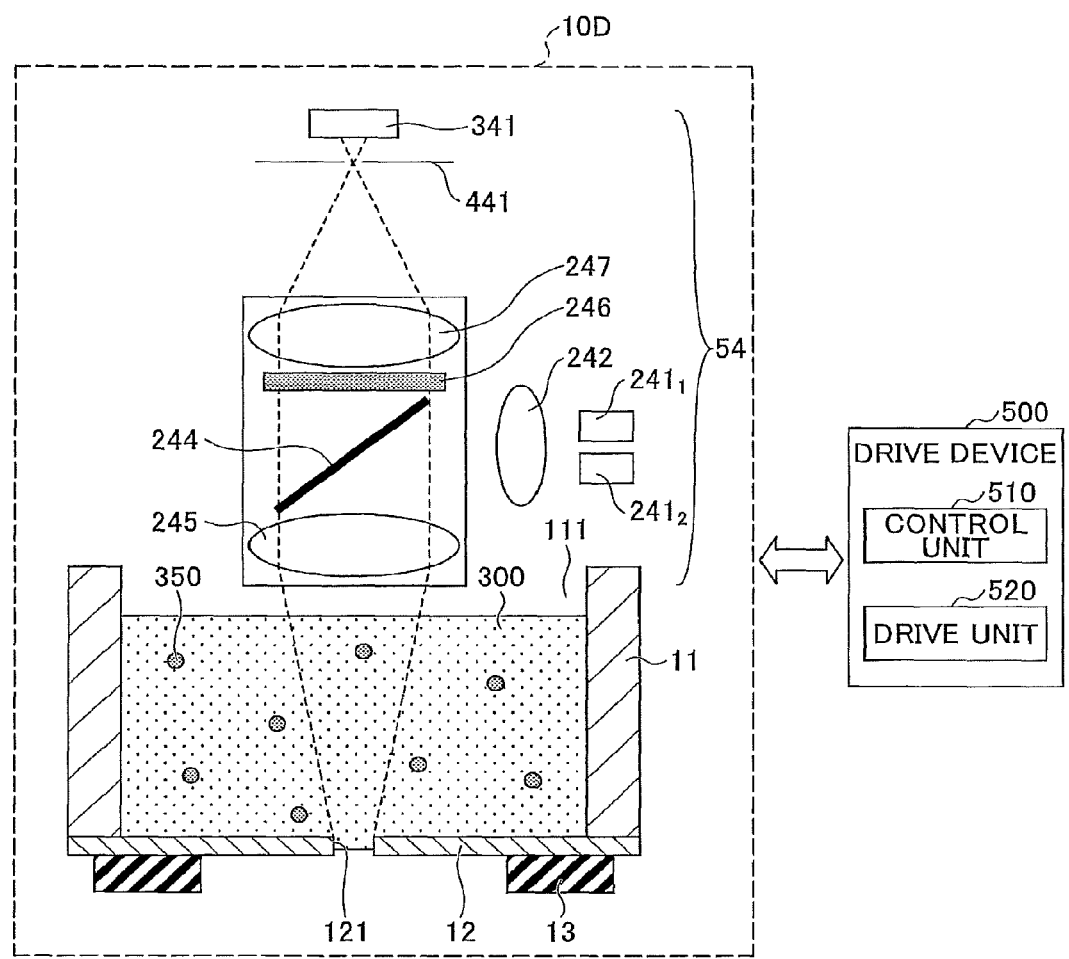
FIG. 10 is a diagram schematically depicting an example of a liquid droplet forming apparatus according to a fourth variation of the first embodiment.

FIG. 10 is a diagram schematically depicting an example of a liquid droplet forming apparatus according to the fourth variation of the first embodiment. Referring to FIG. 10, the liquid droplet forming apparatus 10D is different from the liquid droplet forming apparatus 10C (See FIG. 9) in that the particle state detection unit 44 is replaced by a particle state detection unit 54. The precipitated particle 350 is a florescent particle in the same way as the second variation of the first embodiment.

The liquid droplet forming apparatus 10D includes light sources $241_1$ and $241_2$, wavelengths of which are different from each other. For example, by using LEDs of different wavelengths for the light sources $241_1$ and $241_2$ and by performing illumination in time division, a plurality of kinds of cells can be counted distinctively.

Figure 11:
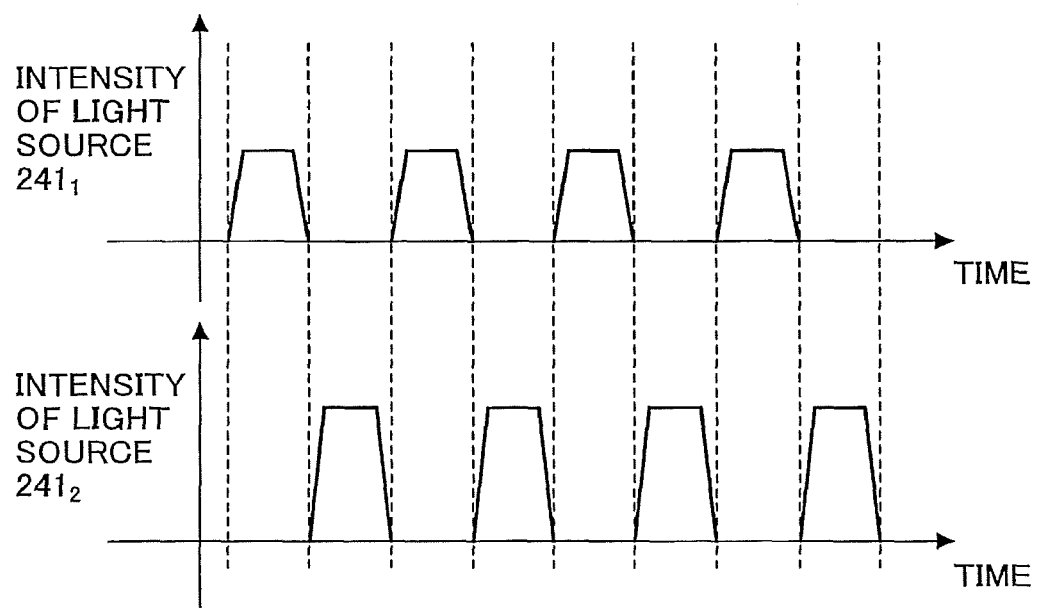
FIG. 11 is a diagram depicting an example of timings of lighting serially two light sources in temporal sequence.

For example, assume that the light source $241_1$ can excite a specific particle "A" and the light source $241_2$ can excite a particle "B" that is different from the particle "A". At this time, as illustrated in FIG. 11, by turning on the light source $241_1$ and the light source $241_2$ serially in time series, numbers of the particle "A" and the particle "B" can be measured.

For example, in the same way as the second variation of the first embodiment, a first threshold and a second threshold are set in advance. Therefore, when, upon tuning on the light source $241_1$, signal intensity indicates a value between the first threshold and the second threshold, a state where only one particle "A" exists around the nozzle 121 can be detected. Moreover, when, upon turning on the light source $241_2$, signal intensity indicates a value between the first threshold and the second threshold, a state where only one particle "B" exists around the nozzle 121 can be detected.

In addition, by using three or more light sources, wavelengths of which are different from each other, numbers of three or more kinds of particles can be measured. Moreover, instead of using a plurality of light sources, wavelengths of which are different from each other, by arranging behind the pinhole 441 a plurality of light receiving elements, which are provided with different wavelength filters, numbers of plurality of kinds of particles can be detected.

In this way, in the fourth variation of the first embodiment, the plurality of light sources are illuminated in time division. Therefore, in addition to the effect of the third variation of the first embodiment, the following effect is achieved. That is, in the liquid droplet forming apparatus 10D, numbers of a plurality of kinds of particles can be detected.

<Fifth Variation of First Embodiment>

In a fifth variation of the first embodiment, an example of a liquid droplet forming apparatus 10, which is used for a system that dispenses a cell in each well, will be described. In the fifth variation of the first embodiment, an explanation for the same component as that in the embodiment, which has already been explained, may be omitted.

Figure 12:
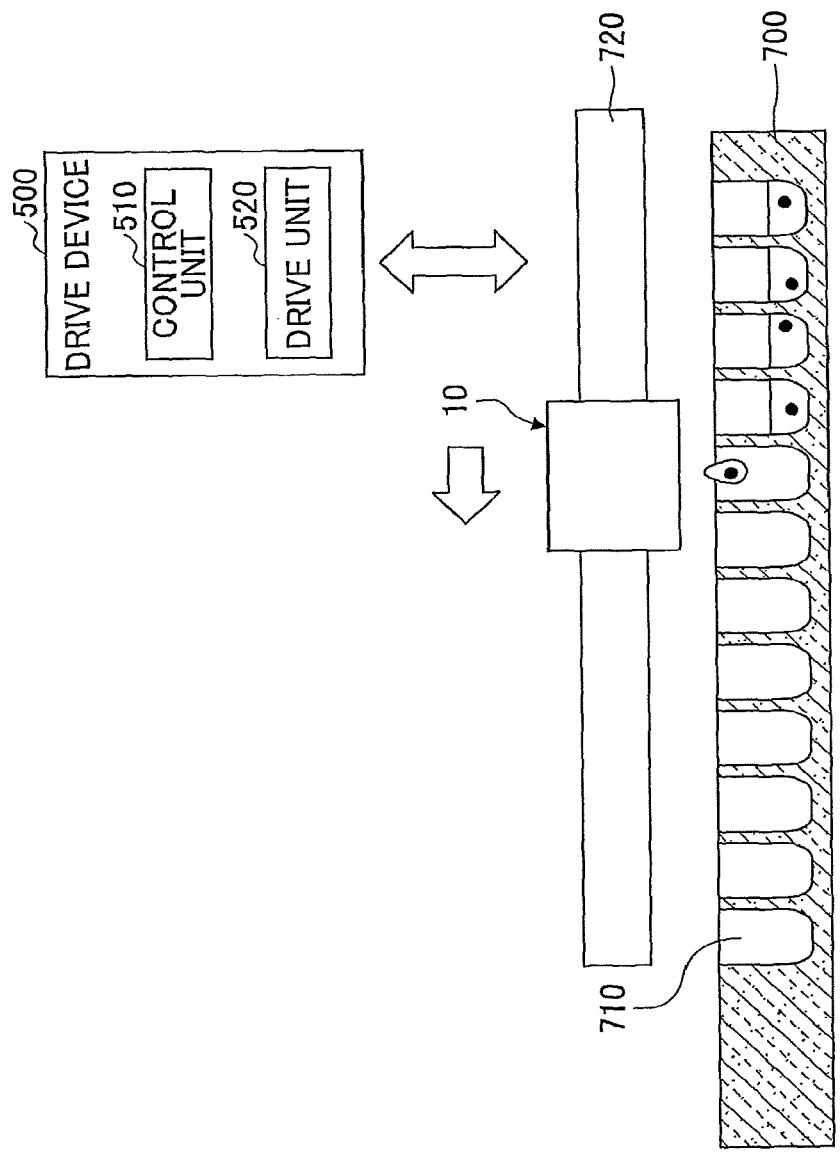
FIG. 12 is a diagram schematically depicting an example of a liquid droplet forming apparatus according to a fifth variation of the first embodiment.

FIG. 12 is a diagram schematically depicting an example of the liquid droplet forming apparatus according to the fifth variation of the first embodiment. Referring to FIG. 12, the liquid droplet forming apparatus 10 is movable along a stage 720.

In a base material 700 that is a droplet arrival object unit, a lot of wells 700 (holes) are formed. The system can discharge particle suspension liquid including a cell into each well 710 serially from the liquid droplet forming apparatus 10.

The liquid droplet forming apparatus 10 discharges solution including a cell into the well 710 by combining appropriately the discharge operation and the agitation operation following, for example, to the flowchart illustrated in FIG. 6. After discharging, the liquid droplet forming apparatus 10 moves along the stage 720 to a position where next well 710 is formed, and executes again the process of the flowchart illustrated in FIG. 6. By repeating the above-described operation, a cell can be dispensed into each of a lot of wells 710.

A function of moving the liquid droplet forming apparatus 10 along the stage 720 to a predetermined position can be incorporated, for example, as a program in the control unit 510 of the drive device 500. In addition, instead of the liquid droplet forming apparatus 10, any of the liquid droplet forming apparatuses 10A to 10D may be used.

As described above, the present invention is explained based on the respective embodiments. However, the present invention is not limited to these embodiments, but various variations and modifications may be made without departing from the scope of the present invention.

For example, when XY-directions are defined on a plane of the membrane 12 that is not deformed and a normal direction of the membrane 12 is defined as a Z-direction, a mechanism that can move the liquid droplet forming apparatus 10 in the X-direction, Y-direction and Z-direction independently may be provided. Therefore, patterning of cells in the XY-plane or laminating of cells in the Z-direction can be performed easily.

What is claimed is:

1. A liquid droplet forming apparatus comprising:
    a liquid retention chamber configured to retain particle suspension liquid in which precipitated particles are suspended;
    a membrane member, in which a nozzle is formed, configured to discharge the particle suspension liquid retained in the liquid retention chamber, as a liquid droplet, by vibration from the nozzle; and
    a particle state detector configured to detect, from a direction that faces a liquid droplet discharging direction with respect to the membrane member, a particle state of the precipitated particle around the nozzle in the particle suspension liquid.

2. The liquid droplet forming apparatus according to claim 1,
    wherein the particle state detector includes a light source and a light receiving unit, and
    the particle state detector is configured to detect scattering light or fluorescence from the precipitated particle around the nozzle, the precipitated particle being irradiated with light from the light source.

3. The liquid droplet forming apparatus according to claim 2,
    wherein the particle state detector is configured to detect, based on an amount of light that the light receiving unit receives, at least one of presence or absence of the precipitated particle around the nozzle, a number of the precipitated particles, and a density of the precipitated particles.

4. The liquid droplet forming apparatus according to claim 2,
    wherein the particle state detector includes an imaging optical element, and
    wherein the light receiving unit and the nozzle are arranged so that by the imaging optical element the light receiving unit and the nozzle are made conjugate to each other.

5. The liquid droplet forming apparatus according to claim 4,
    wherein the light receiving unit is a light receiving element for one pixel, wherein a pinhole is provided immediately before the light receiving element, and wherein the pinhole and the nozzle are arranged so that by the imaging optical element a hole provided in the pinhole and the nozzle are made conjugate to each other.

6. The liquid droplet forming apparatus according to claim 1, wherein the particle suspension liquid is solution in which cells are suspended.

7. The liquid droplet forming apparatus according to claim 1, wherein the liquid droplet is formed based on a detection result by the particle state detector.

8. The liquid droplet forming apparatus according to claim 1, wherein the particle suspension liquid retained by the liquid retention chamber is agitated based on a detection result by the particle state detector.

9. The liquid droplet forming apparatus according to claim 1, wherein the nozzle and around the nozzle are viewable before discharging the liquid droplet.

\* \* \* \* \*